US00PP27578P3

(12) United States Plant Patent
Cain

(10) Patent No.: US PP27,578 P3
(45) Date of Patent: Jan. 24, 2017

(54) SWEET CHERRY TREE NAMED 'IFG CHER-ONE'

(50) Latin Name: *Prunus avium*
Varietal Denomination: IFG Cher-one

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 60 days.

(21) Appl. No.: 14/545,349

(22) Filed: Apr. 27, 2015

(65) Prior Publication Data

US 2016/0316597 P1 Oct. 27, 2016

(51) Int. Cl.
*A01H 5/08* (2006.01)

(52) U.S. Cl.
USPC ..... Plt./181

(58) Field of Classification Search
USPC ..... Plt./181
See application file for complete search history.

*Primary Examiner* — Susan McCormick Ewoldt

(57) ABSTRACT

This invention is a new and distinct sweet cherry variety denominated 'IFG Cher-one'. The new sweet cherry is characterized by producing very large dark red kidney shaped fruits having broad shoulders and flat to round base. Fruits ripen early about three days ahead of the 'Brooks' variety.

1 Drawing Sheet

Latin name of the genus and species claimed: *Prunus avium.*

Variety denomination: 'IFG Cher-one'.

BACKGROUND OF THE INVENTION

The new and distinct sweet cherry tree described and claimed herein originated from open pollinated seeds collected in May 2001, from a sweet cherry tree designated as '10-1' growing in a commercial orchard of the 'Brooks' variety (U.S. Plant Pat. No. 6,676) growing near Delano, Kern County, Calif. The seeds were stratified, germinated and the resulting seedlings were planted in a field located near Delano, Kern County, Calif. in April 2002. The present variety of sweet cherry tree was selected as a single plant in May 2005 and was first asexually propagated in January 2006 by grafting onto a tree of 'Belle de Planchoury' (not patented), itself being grafted on *Prunus mahalab* rootstock. It was subsequently propagated directly onto *Prunus mahalab* rootstock by chip budding in April 2007. These propagules were found to reproduce true-to-type by asexual propagation. All propagation was done near Delano, Kern County Calif.

BRIEF SUMMARY OF THE INVENTION

Sweet cherries have traditionally been grown in climates with long cold winters and cool to moderately warm summers. Such climates provide enough cold winter temperatures to allow normal growth to resume in the spring and summer temperatures that are low enough not to induce production of unmarketable double or spurred fruit, but it limits the seasonality that cherries are available. The sweet cherry breeding program focuses on developing types of cherries that will grow in regions with low winter chilling and high summer temperatures so that the fruit will ripen before fruit in traditional growing regions.

The new sweet cherry tree 'IFG Cher-one' is characterized by producing very large dark red kidney shaped fruits having broad shoulders and flat to round base. Fruits ripen early about three days ahead of the 'Brooks' variety. The 'IFG Cher-one' has somewhat soft acidic flesh. Firmness can be improved by application of gibberellic acid. The tree has a medium high chilling requirement similar to or slightly lower than the 'Brooks' variety. It produces a similar number of doubled and spurred fruits as the 'Brooks' variety in high summer temperature regions such as the Southern San Joaquin Valley of California. Fruits of 'IFG Cher-one' have medium long, thick stems that remain attached and stay green during storage and shipping.

In comparison to the 'Brooks' variety, which is a major variety grown in warm regions, the present variety ripens about three days earlier, is larger and has more desirable darker red skin and flesh. In comparison to its female parent, pollenizer tree designated as '10-1', the present variety has a lower chilling requirement and exhibits less undesirable symptoms of lack of chill including more consistently setting crops, exhibiting less undesirable variable ripening and producing fewer unmarketable doubled or spurred fruits.

In comparison to the 'Tulare' variety (U.S. Plant Pat. No. 6,407), the 'IFG Cher-one' produces larger fruit that ripen approximately six to eight days before the 'Tulare' variety. The fruit shape of 'IFG Cher-one' has a more desirable round to kidney shape with broad shoulders and flat stylar end compared to the more pointed, narrower shoulder shape of the 'Tulare' variety. The 'IFG Cher-one' has a higher chill requirement and produces more doubled fruits than the 'Tulare' variety.

BRIEF DESCRIPTION OF THE DRAWING

The accompanying photographic drawing in FIG. 1 illustrates in full color 'IFG Cher-one'. The photograph was taken outdoors with indirect lighting. The colors are as nearly true as is reasonably possible in a color representation of this type. An actively growing shoot tip collected at harvest can be seen in the upper portion of the drawing. Typical mature fruit and fruit in cross-section are displayed on the lower half of the drawing. Typical cleaned and dried fruit pits are displayed on the right lower half of the drawing.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2001 by The Royal Horticultural Society, London, England.

Throughout this specification subjective description values conform to those set forth by the International Board for Plant Genetic Resources (IBPGR) 'Cherry Descriptor List' (*Prunus* spp.) (1985) which was developed with full support from the Commission of the European Communities (CEC) Programme Committee for Plant Disease Resistance Breeding and the Use of Genebanks.

The descriptive matter which follows pertains to an 'IFG Cher-one' plant growing on its own roots grown in the vicinity of Delano, Kern County, Calif. during 2013 and 2014, and is believed to apply to plants of the variety grown under similar conditions of soil and climate elsewhere:

TREE

General:

*Age*.—11 yrs. old.
*Height*.—About 2.3 M.
*Width*.—About 3.2 M.
*Vigor*.—Vigorous.
*Density of foliage*.—Dense.
*Form*.—Spreading.
*Root stock*.—Own root.
*Resistance to*.—Insects: Average typical of *Prunus avium* species. Diseases: Average typical of *Prunus avium* species.
*Chilling*.—Medium, similar to 'Brooks'.
*Graft compatibility*.—Good; produces compatible graft unions with *Prunus avium*, 'Mazzard' seedlings (non-patented) and *Prunus mahaleb* seedlings (non-patented).

Trunk:

*Trunk diameter of* 12 *year old trees,* 30 cm *above the soil line*.—About 19.9 cm.
*Lenticel size*.—Large.
*Lenticel dimensions*.—Length: About 1.3 cm. Width: About 0.3 cm.
*Lenticel shape*.—Elliptical shape oriented horizontally.
*Lenticel color*.—The following colors were observed: Greyed-white: 156A and C.
*Trunk surface texture*.—Rough.
*Outer bark color*.—The following colors were observed: Greyed-orange: 187B and 183B and Greyed-green: 198C.

BRANCHES

1 Year old wood:

*Vertical top growth length*.—Long; About 146.4 cm.
*Horizontal growth length*.—Medium: About 47.7 cm.
*Diameter*.—Vertical growth: About 1.6 cm. Horizontal growth: About 0.9 cm.
*Internode length*.—Medium: About 3 cm.
*Number of lenticels*.—Few.
*Lenticel size*.—Small.
*Lenticel dimensions*.—Length: About 1 mm. Width: About 2 mm.
*Lenticel shape*.—Round.
*Bark color*.—The following colors were observed: Greyed-orange: 175A and 166B.

2 *Year old wood:*

*Length*.—About 51.0 cm.
*Diameter*.—About 1.1 cm.
*Internode length*.—About 3.2 cm.
*Number of lenticels*.—Medium dense.
*Lenticel dimensions*.—Length: About 5 mm. Width: About 1 mm.
*Lenticel shape*.—Elliptical shape oriented horizontally.
*Bark color*.—The following colors were observed: Greyed-orange: 177A and 165A and 164A.

BUDS

Vegetative buds:

*Shape*.—Elongated.
*Vegetative bud dimensions*.—Length: About 7 mm. Width: About 3 mm.
*Vegetative bud burst*.—Feb. 25, 2014.

Flower buds:

*Flower bud dimensions*.—Length: About 10.6 mm. Width: About 7.1 mm.
*Shape*.—Oval.
*Placement*.—At bud positions mostly 1 to 6 on 1-year wood.
*Average number of flower buds on first year wood*.—About 3.4.
*Number of flower buds per spur on second year wood*.—2 to 7. Average: About 4.6.
*Color*.—The following colors were observed: Yellow-green: 144A and B.
*Flower bud burst*.—Feb. 25, 2014.

LEAVES

Mature leaves:

*Leaf dimensions*.—Length; About 16.9 cm. Width: About 8.3 cm.
*Leaf shape*.—Elliptic: Symmetric on both sides of central axis.
*Shape of tip*.—Acute: broadly.
*Shape of base*.—Oblique.
*Margin*.—Serrated: regular.
*Surface texture*.—Smooth.
*Leaf profile*.—Involute.

Upper surface:

*Upper surface pubescence*.—None.
*Upper leaf surface color*.—Yellow-green: 147A.

Lower surface:

*Lower surface pubescence*.—All over; medium dense.
*Lower leaf surface color*.—Yellow-green: 147B.

Petiole:

*Petiole dimensions*.—Length: About 3.0 cm. Width: About 2.8 cm.
*Upper surface of petiole color*.—Greyed-orange: 177A.
*Lower surface of petiole color*.—Greyed-orange: 166A.
*Petiole groove*.—Wide.
*Petiole pubescence*.—Only on lower surface; sparse to medium.
*Venation*.—Arcuate.
*Vein color*.—Yellow-green: 145C.

Glands:

*Number of glands.*—1 to 2.

*Gland dimensions.*—Length: About 3.3 mm. Width: About 2 1 mm.

*Gland shape.*—Reniform.

*Gland location.*—On petiole.

*Gland color.*—The following colors were observed: Orange-red: N34 and Yellow-green: 153A.

*Leaf stipule.*—Not present.

FLOWERS

*Blooming period.*—Mid-season.

*Blooming dates.*—First bloom: Mar. 5, 2013. Full bloom Mar. 15, 2013.

*Number of flowers per cluster.*—2 to 4. Average: About 2.5.

*Corolla.*—Composed of unfused petals, somewhat overlapping.

*Corolla diameter.*—About 3.3 cm.

*Petal number.*—5.

*Petal length.*—About 1.8 cm.

*Petal width.*—About 1.6 cm.

*Margin waviness.*—Weak.

*Division of upper margin.*—Notched.

*Color of petal upper surface.*—White: 155D.

*Color of petal lower surface.*—White: 155D.

*Peduncle.*—Length: About 1.1 cm. Width: About 0.12 cm.

*Peduncle color.*—Yellow-green: 144A.

*Number of sepals.*—5.

*Sepal length.*—About 0.6 cm.

*Sepal width.*—About 0.5 cm.

*Sepal shape.*—Triangular.

*Sepal color.*—Upper surface: Yellow-green: 144C. Lower surface: Red-purple 60C.

*Filament.*—Length: About 0.6 to 1.5 cm. Width: About 0.03 cm.

*Filament color.*—White: 155D.

*Anther color.*—Yellow-orange: 17C.

*Pollen color.*—The following colors were observed: Greyed-yellow: 162A and Greyed-orange: 163A.

*Pollen production.*—Medium.

*Flower compatibility group.*—S6S9.

FRUIT

General:

*Ripening period.*—Early midseason about 3 days before 'Brooks': Approximately: May 3, 2013.

*Use.*—Fresh market.

*Keeping quality.*—Average: Similar to 'Brooks' variety.

*% Titratable acidity.*—About 0.70%.

*Refractometer test.*—Soluble solids: Brix — About 14.4.

*Firmtech II* (g/mm).—About 311.

*Flavor.*—Average, slightly acidic.

*Juice color.*—Greyed-purple: 187A.

*Juice amount.*—Intermediate.

*Eating quality.*—Average.

Stem:

*Stem.*—Length: About 2.8 cm. Width: About 0.17 cm.

*Stem color.*—Yellow-green: 144A.

*Stem cavity.*—Wide.

*Stem retention during storage.*—Very good.

*Stem storage quality.*—Good.

Berry:

*Uniformity of size.*—Uniform.

*Shape.*—Kidney: Broad, square shoulders with flat to round stylar ends.

*Fruit weight.*—About 10.1 gm.

*Apical diameter.*—About 26.7 mm.

*Diameter transversely across suture.*—About 21 7 mm.

*Diameter at right angle to suture plane.*—About 26.7 mm.

*Suture.*—None.

*Percent of excessively deep or split sutures.*—About 0%.

*Doubles.*—About 16%, similar to 'Brooks'.

Skin:

*Thickness.*—Medium.

*Texture.*—Mostly smooth, with very little indentation noted at lenticels.

*Skin color.*—The following colors were observed: Red-purple: 59A and B and C.

*Tendency to tip crack.*—Not susceptible.

*Tendency to stem cavity crack.*—Not susceptible.

Flesh:

*Texture.*—Soft.

*Color.*—The following colors were observed: Greyed-purple: 187A and B.

Stone:

*Shape.*—Oblong.

*Stone dimensions.*—Length: About 12 mm. Width: About 8 mm.

*Type.*—Clingstone.

*Surface texture.*—Smooth.

*Stone color when dry.*—Orange-white: 159B.

*Tendency to split.*—None.

*Shape.*—Round to slightly ovate.

*Base.*—Flat.

*Apex.*—Rounded.

*Ventral edge.*—Narrow suture subtended by 2 somewhat prominent ridges converging at base and apex.

*Dorsal edge.*—Smooth, narrow ridge from base to apex.

What is claimed:

1. A new and distinct variety of sweet cherry tree as herein illustrated and described.

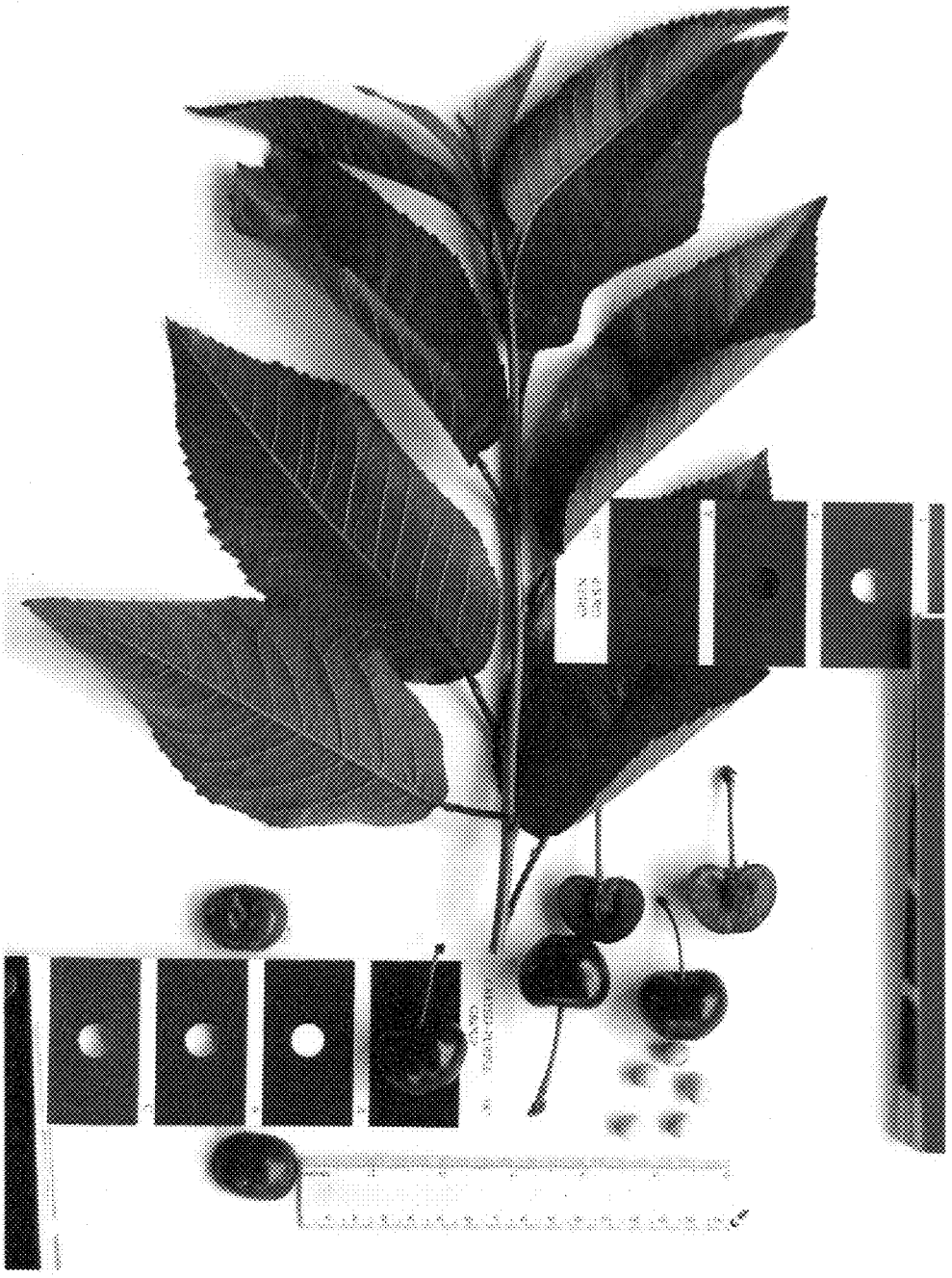

* * * * *